US010611853B1

(12) United States Patent
Frazer

(10) Patent No.: US 10,611,853 B1
(45) Date of Patent: Apr. 7, 2020

(54) ASSESSING AND IMPROVING WHEAT GLUTEN QUALITY WITH RHEOMETRIC ANALYSIS

(75) Inventor: Scott R. Frazer, Maple Grove, MN (US)

(73) Assignee: Ardent Mills, LLC, Denver, CO (US)

( * ) Notice: Subject to any disclaimer, the term of this patent is extended or adjusted under 35 U.S.C. 154(b) by 1519 days.

(21) Appl. No.: 12/415,277

(22) Filed: Mar. 31, 2009

Related U.S. Application Data

(60) Provisional application No. 61/041,571, filed on Apr. 1, 2008.

(51) Int. Cl.
*G01N 33/10* (2006.01)
*C08B 30/04* (2006.01)

(52) U.S. Cl.
CPC ........... *C08B 30/046* (2013.01); *G01N 33/10* (2013.01)

(58) Field of Classification Search
CPC ........ G01N 11/00; G01N 11/02; G01N 11/10; G01N 33/10; A21D 2/186; A21D 13/04; A21D 8/00; A21D 2/265; A21D 2/00; A23J 3/14; A23J 3/18; A23J 1/12; C08B 30/046; A23V 2250/5118; A23V 2250/5486; A21C 1/145
USPC ...................... 426/231, 94, 549, 622; 73/169
See application file for complete search history.

(56) References Cited

U.S. PATENT DOCUMENTS

| | | | | |
|---|---|---|---|---|
| 2,961,353 | A * | 11/1960 | Carlson et al. | 127/67 |
| 3,790,553 | A * | 2/1974 | Rao et al. | 530/375 |
| 3,951,938 | A * | 4/1976 | Kerkkonen et al. | 530/374 |
| 4,007,289 | A * | 2/1977 | Jaeckering | 426/549 |
| 4,076,845 | A * | 2/1978 | Johannson | 426/19 |
| 4,910,297 | A * | 3/1990 | Zawistowska | 530/375 |
| 5,547,690 | A * | 8/1996 | Vaisanen et al. | 426/10 |
| 7,604,929 | B2 | 10/2009 | Dryden et al. | |
| 2009/0061055 | A1 * | 3/2009 | Newcomb et al. | 426/231 |

OTHER PUBLICATIONS

Quality management manual for production of high quality cassava flour. / Dziedzoave, Nanam Tay; Abass, Adebayo Busura; Amoa-Awua, Wisdom K.; Sablah, Mawuli; Adegoke, Gabriel O. (Editor); Brimer, Leon (Editor). Ibadan, Nigeria : International Institute of Tropical Agriculture (IITA), 2006.*
US Dept. of Agriculture, Experiment Station Record, vol. XXXIX, Jul.-Dec. 1918.*
Petrofsky, Rheological Properties of Dough Made with Starch and Gluten from Several Cereal Sources, Cereal Chem. 72(1):53-58. 1994.*
Apichartsrangkoon, Dynamic Viscoelastic Behavior of High-Pressure-Treated Wheat Gluten, Sep./Oct. 1999, vol. 76, No. 5 pp. 777-782, http://dx.doi.org/10.1094/CCHEM.1999.76.5.777.*
Little et al, Changes in Soy Proteins during Heating Analyzed by Pressure Rheometry (Year: 1996).*
Decision dated Jul. 5, 2016 entered in *Rapid Litigation Management Ltd. et al.* v. *Cellzdirect, Inc.*, U.S. Court of Appeals, Case No. 2015-1570.

\* cited by examiner

*Primary Examiner* — Erik Kashnikow
*Assistant Examiner* — Lela S. Williams
(74) *Attorney, Agent, or Firm* — Faegre Drinker Biddle & Reath LLP

(57) ABSTRACT

Disclosed herein is a method of assessing rheology characteristics of vital wheat gluten to determine how to improve the quality of VWG product and the choice of VWG for a particular product.

16 Claims, 6 Drawing Sheets

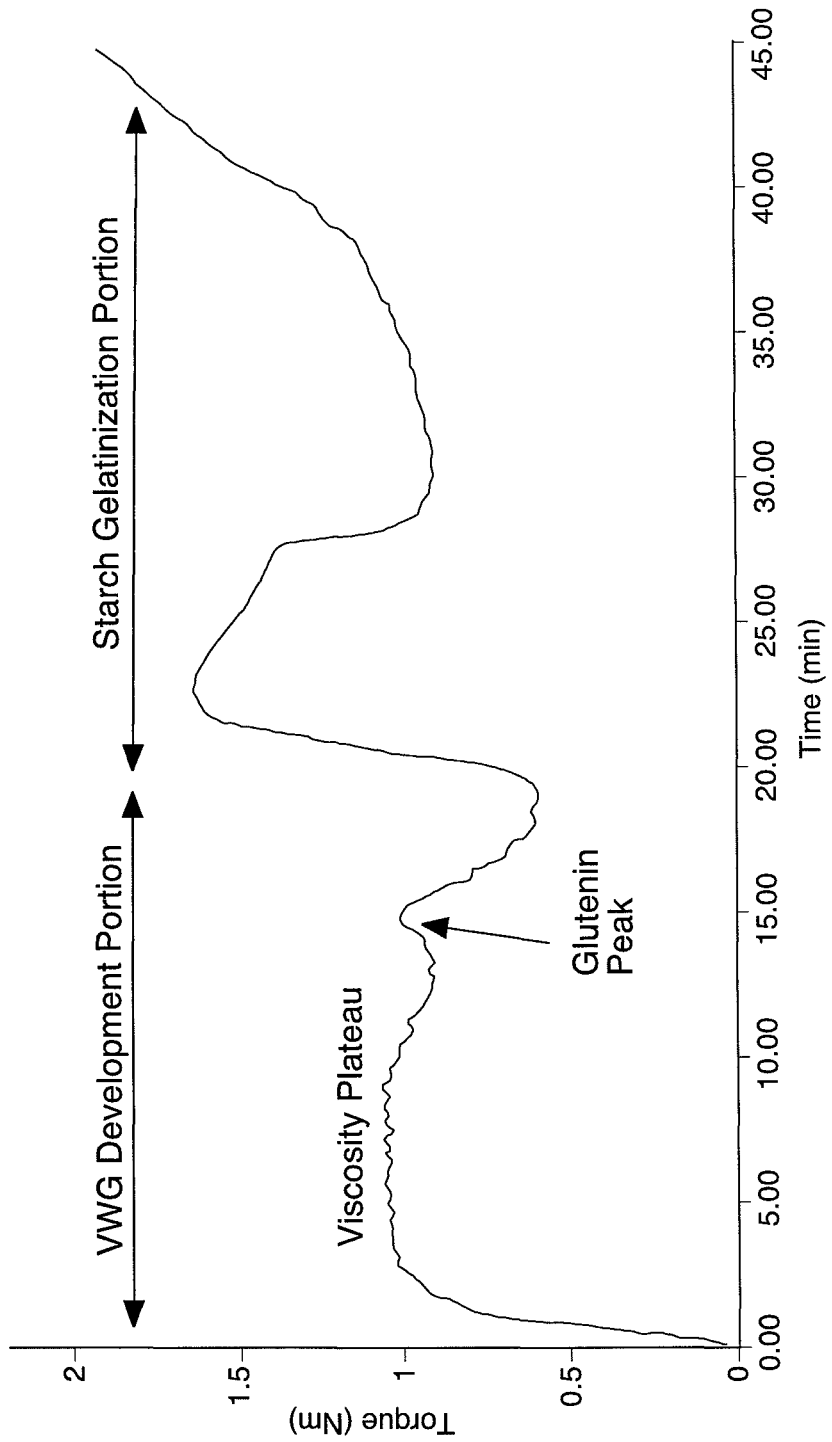

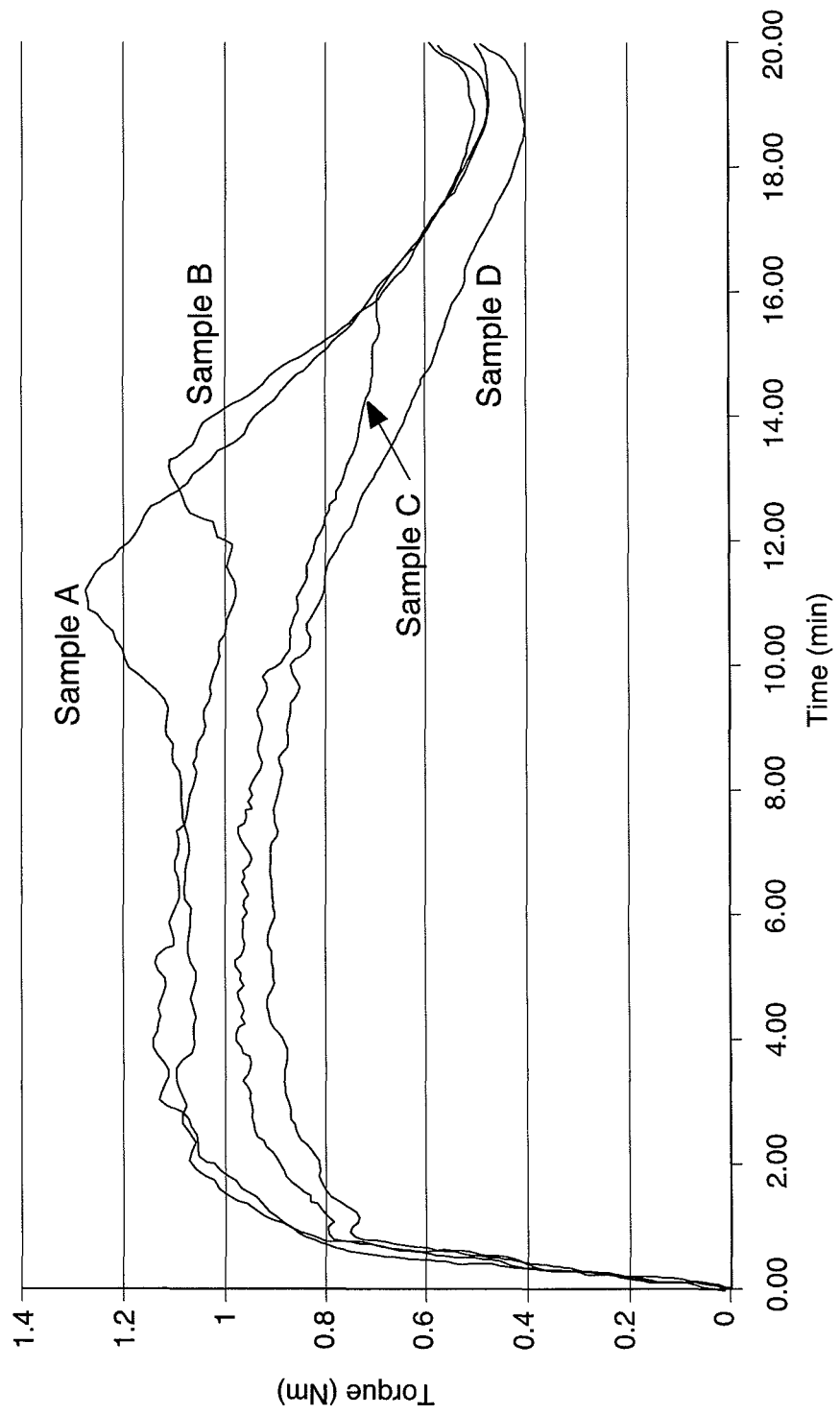

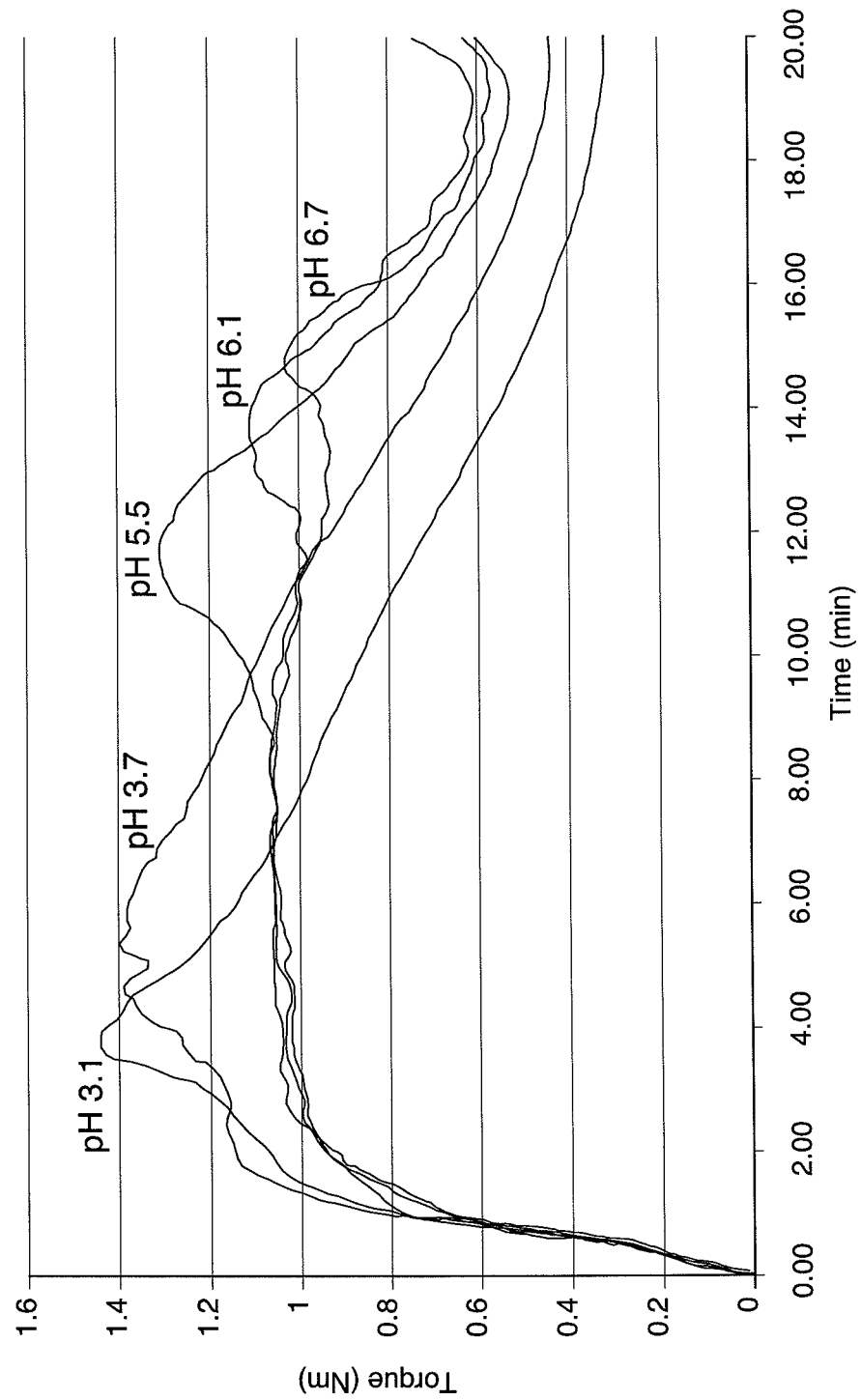

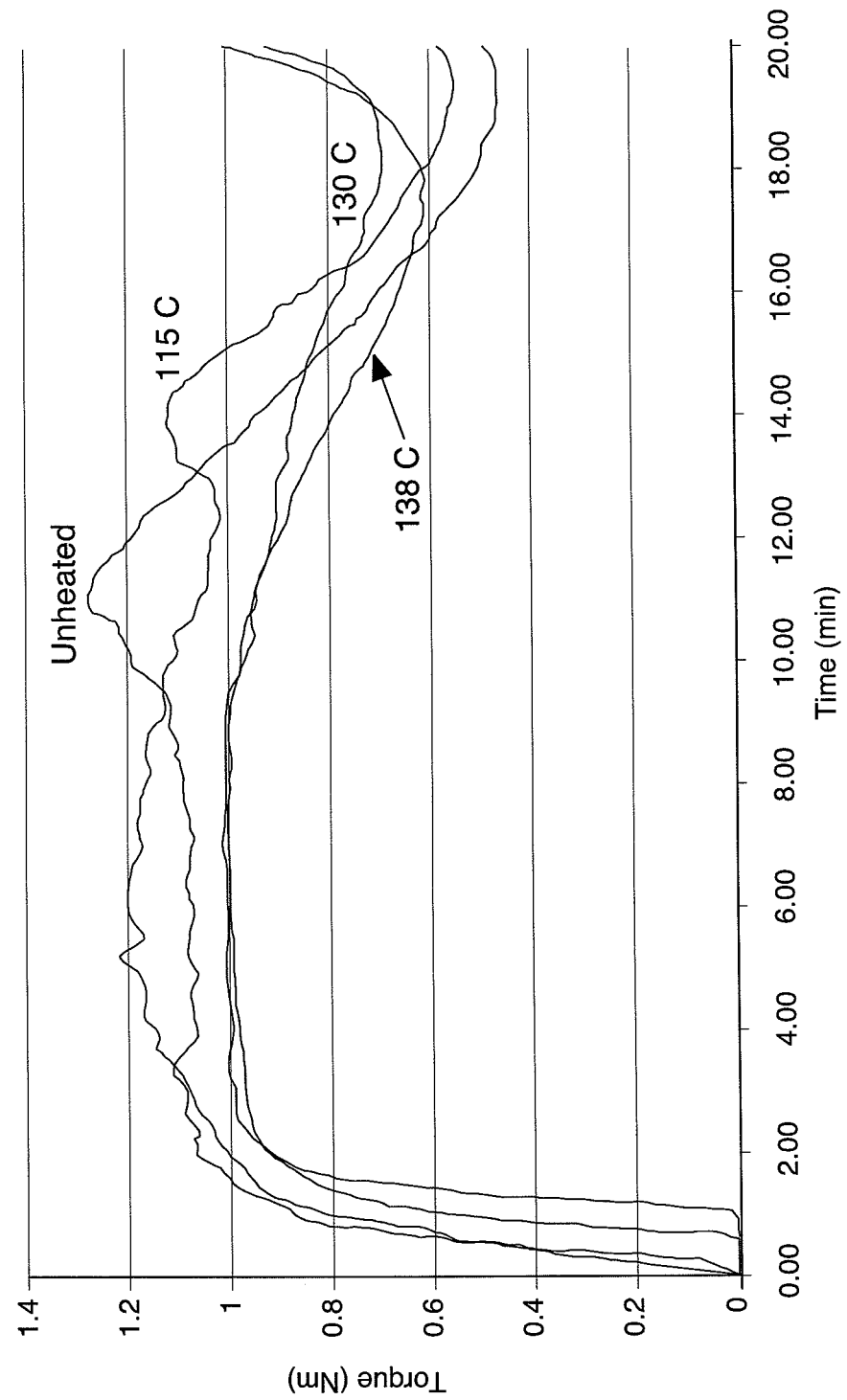

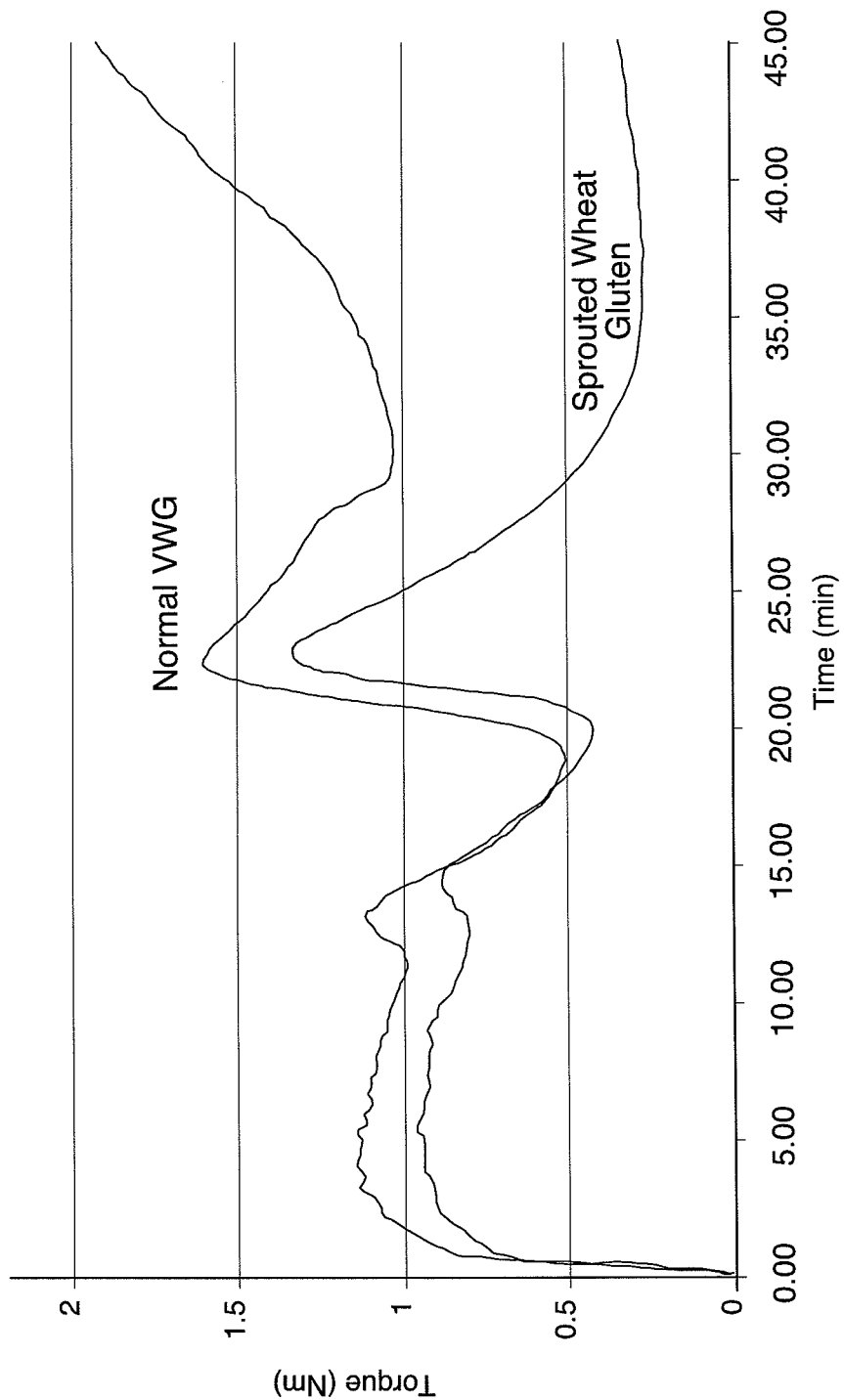

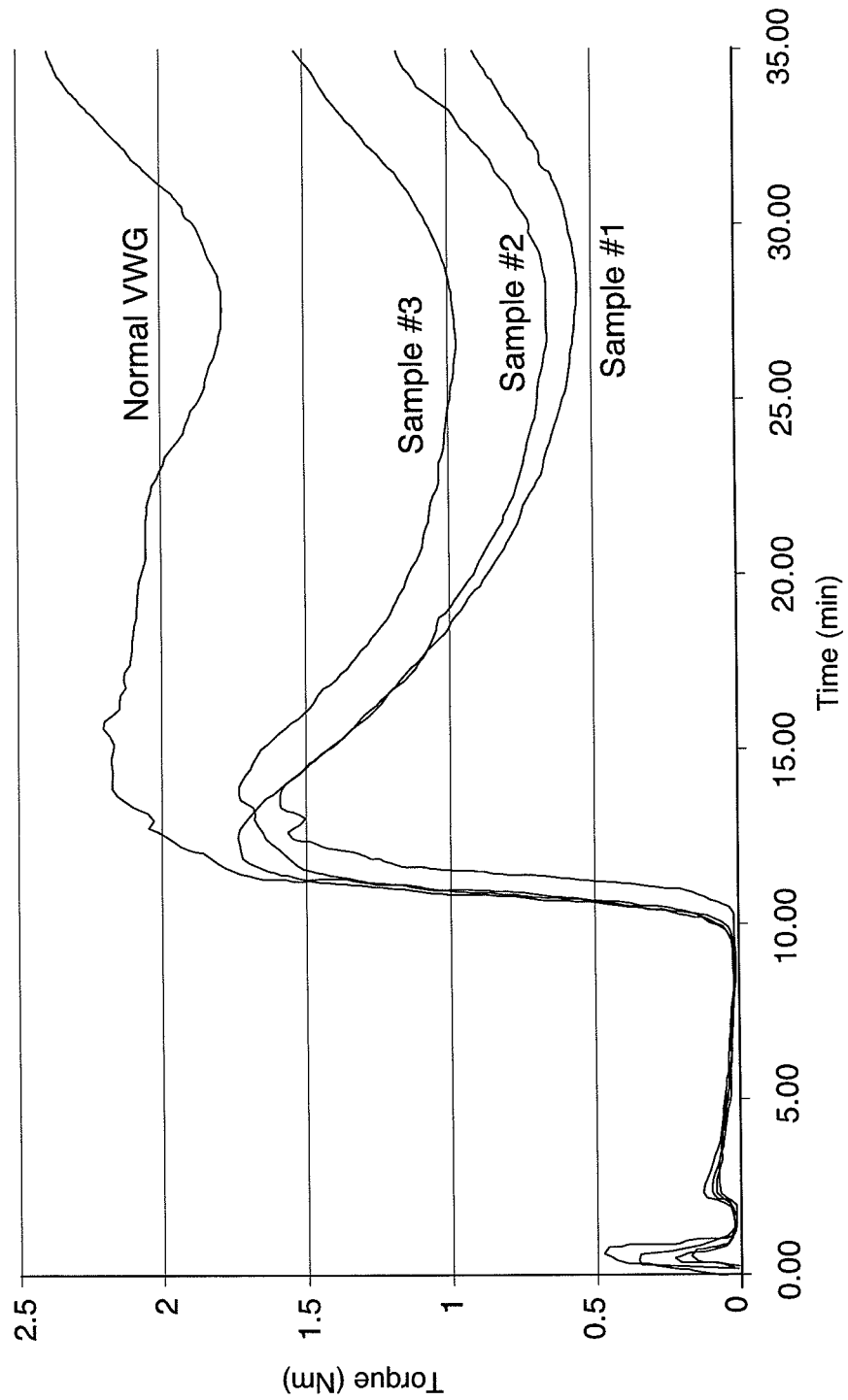

ASSESSING AND IMPROVING WHEAT GLUTEN QUALITY WITH RHEOMETRIC ANALYSIS

This application claims the benefit of U.S. Provisional application Ser. No. 61/041,571 filed 1 Apr. 2008 entitled ASSESSING AND IMPROVING WHEAT GLUTEN QUALITY WITH RHEOMETRIC ANALYSIS, which is hereby incorporated by reference in its entirety.

FIELD

Disclosed herein is a method of assessing rheology characteristics of vital wheat gluten to determine how to improve the quality of that product.

INTRODUCTION

Vital wheat gluten (VWG) is the protein in wheat flour that enables dough to rise and bread to have a soft texture. If the VWG in flour is poor or damaged, loaf volumes will be low and the bread will have a dense texture. Therefore, VWG is added to many bread formulas to assure good loaf quality. Flour with good gluten quality is said to have a good strength, while flour with poor gluten quality is weak.

VWG is isolated from wheat flour in a process that washes out the wheat starch, leaving the gluten protein behind. After further purification steps the gluten is dried. The quality of the resulting gluten product will depend upon first, the initial quality of the gluten in the wheat flour used as the raw material and secondly, upon the process used in extracting that gluten.

There are several methods to determine the quality of gluten. For example, a % protein measurement can be taken and, for most commercial glutens, this usually runs between 75-85%. This value does not, however, reveal the quality of the gluten. For example, the gluten could be fully denatured, but still give the same apparent protein concentration. Another method, called gluten index, determines the amount of gluten that does not wash away during a water wash and centrifugation. This method gives further information, but does not always correlate with bread quality. Therefore, in order to test gluten quality many manufactures bake test loaves of bread, which is a time consuming process.

SUMMARY

Disclosed herein are methods of determining the quality of VWG with rheometric methods and for determining how to improve that VWG quality. Processing conditions that can reduce the quality of VWG are also specified and rheometric methods are provided to determine when damage is occurring.

The method provided in the disclosure includes determining the quality of vital wheat gluten (VWG) in a sample mixture containing VWG of unknown quality by comparing a rheometric profile from a standard mixture made with high quality VWG to the rheometric profile of the sample mixture. The standard mixture and the sample mixture are made to include the same ratio of VWG:Starch and the same amount of water. In some examples, the standard mixture is made using a VWG that has been processed and tested and shown to be good for a particular purpose, such as for use in bread dough, buns, cereal, cookies, muffins, cakes, noodles or pizza dough. The differences, or lack of differences, between the rheometric profiles of the standard mixture and sample mixture can be used to determine if the VWG in the sample mixture will perform well for a specific end purpose or it was processed in such a way that the VWG was damaged.

One of ordinary skill in the art will appreciate that the standard mixture and the sample mixture can be made in various ratios of VWG to starch by weight. In some examples the ratio of VWG to wheat starch is about 10% VWG:90% wheat starch. In other examples the ratio of VWG to wheat starch is between 10% VWG:90% wheat starch and 80% VWG:20% wheat starch. In yet other examples, the ratio of VWG to wheat starch is about 40% VWG:60% wheat starch.

In some examples the rheometric profile comprises a VWG development portion having a glutenin viscosity peak. The timing and strength of the glutenin viscosity peak of the standard mixture can be compared to that of the sample mixture and differences can indicate that the pH of the VWG in the sample mixture was process using low pH conditions.

In other examples, the timing and strength of the glutenin viscosity peak of the standard mixture can be compared to that of the sample mixture and the difference can indicate that VWG was heated during processing and damaged.

In other examples, the rheometric profile includes a starch gelatinization portion and the starch gelatinization portion of a standard mixture can be compared to the starch gelatinization portion of a sample mixture. Differences between the rheometric profiles can indicate that the VWG in the sample mixture contains enzymes that break down the starch, such as amylases. VWG that is made from wheat that has sprouted typically has an increased amount of amylase.

The disclosure also provides methods of making quality vital wheat gluten which include contacting vital wheat gluten with an aqueous solution having a pH to separate the starch from the gluten, drying the wheat gluten using a certain temperature, testing the vital wheat gluten by comparing the VWG made by the process to a standard VWG:Starch mixture as described above, and adjusting the pH and/or the drying temperature. Typically, pH can be adjusted by changing the wash water to a wash water with neutral pH, or by adding caustic. The foregoing and other features will become more apparent from the following detailed description of several embodiments, which proceeds with reference to the accompanying figures.

FIGURES

FIG. 1 shows an exemplary viscosity profile generated using the MIXOLAB® instrument. In this protocol, VWG, wheat starch, and water are added together at predetermined levels to create a bread dough and the mixing process is initiated. For the first 8 minutes, the mixing cell is held at 30° C. After 8 minutes, the mixing cell temperature is raised at 4° C./minute to a final temperature of 90° C. After 7 minutes at 90° C., the cell temperature is dropped at 4° C./min to 50° C. and held there for 5 minutes. Until the cell temperature reaches ~65° C., the rheology of the bread dough is due to VWG development. At the beginning of VWG development, the VWG absorbs water and starts to build a protein matrix. Strong, high protein flours and good quality VWG/starch mixtures often show a second peak towards the end of the VWG development. It is believed that this peak is the higher molecular weight gluten (glutenin) that requires more mechanical or thermal energy to finally incorporate into the dough. This produces a small viscosity peak, which is hereinafter referred to as the "glutenin" peak for simple identification. The location of this glutenin peak can be very indicative of gluten quality. At 65° C., the starch in the dough begins to gelatinize and becomes the major determiner of dough viscosity. The VWG Development portion, Glutenin peak, and Starch Gelatinization portion are identified FIG. 2 shows the VWG development portion of the viscosity profiles of several VWG samples mixed in a 40:60 ratio with wheat starch. Sample B is an exceptionally high quality VWG. Samples C and D show progressively weaker viscosity profiles.

FIG. 3 shows viscosity profiles of Sample B from FIG. 2 after treatment at the indicated pH levels. The more acidic treatments caused a shift of the Glutenin viscosity peak to earlier times.

FIG. 4 shows viscosity profiles of the Sample A gluten from FIG. 2 after treatment at different temperatures. The higher the temperature of the treatment, the weaker the sample becomes as evidenced by a reduction of the glutenin viscosity peak and its shift to later times. In samples treated at 130° C. and 138° C., the glutenin peak is absent.

FIG. 5 shows the full viscosity profile of a VWG sample taken from sprouted wheat, which is known to have higher than desirable levels of amylase enzymes. The sprouted VWG sample is compared to Sample B from FIG. 2. The severe reduction in viscosity is identified by the change in the strength (nM) of the sprouted sample in the gelatinization portion of the curve.

FIG. 6 shows the viscosity profile of additional sprouted wheat VWG samples. The figure focuses more specifically on the gelatinization portion of the viscosity profile to better quantify the level of amylases present in the gluten, using a mixing cell temperature protocol (described in Example 5) that is different from that shown in all other previous figures.

DETAILED DESCRIPTION

Overview

The disclosure provides methods of determining the quality of vital wheat gluten (VWG), as well as methods of determining the impact of various processing conditions on VWG quality. The methods involve establishing a standard VWG mixture and comparing the viscosity profile of the standard mixture to a sample mixture that includes a VWG of unknown quality. The standard mixture and the sample mixture contain the same ratio of VWG to wheat starch. Since VWG is usually added to wheat flour, in all these examples the starch used is wheat starch, though other starches could be used instead.

In some examples, the standard VWG is chosen because of its performance in specific baking conditions. For example, a VWG that has been shown to produce high quality bread, pizza dough or noodles should be chosen for use as the standard, against which future VWG samples of unknown quality will be compared. Hence, VWG that is specifically useful for noodle, pizza dough or bread manufacturing can be identified.

The disclosure also provides methods of making VWG that include determining the viscosity profile of a VWG being made in a running production operation and comparing that profile to the viscosity profile of a known, typically high-quality, standard VWG mixture. By comparing the profiles of production VWG to the high-quality standard VWG, the processing conditions being used to make the VWG can be adjusted to increase or otherwise select the quality of the VWG being produced. Conditions that can be adjusted include wheat selection, extraction water pH, and drying temperatures.

Analysis of Vital Wheat Gluten

Rheology is the analysis of the viscosity of materials. There are a number of instruments available for determining the viscometry of dough, including the farinograph, mixograph, amylograph, and simple viscometeis. Any instrument that can be used to measure torque (or force) while mixing dough can be used in the method provided. For example, the relatively new instrument called the MIXOLAB® instrument from Chopin Technologies (France) is used in the examples provided, but instruments such as those described above will work as well. These instruments are generally used to measure the viscosity of a flour/water mixture or of a flour blend/water mixture. Described herein are the viscosities of mixtures that include, for example, vital wheat gluten, starch and water. These viscosity measurements are taken while mixing set periods of time and under controlled temperature conditions. These measurements can then be graphed or organized in tables. Exemplary line graphs from the MIXOLAB® machine are provided herein. One of ordinary skill in the art will appreciate that other modes of depicting the information are possible.

To analyze the characteristics of a sample of VWG, the VWG is mixed with water and starch, for example wheat, tapioca, potato, rice starch, or mixtures thereof. To establish a standard data set that can be used for comparison against subsequent samples of VWG, VWG that has performed well for its intended purpose, for example VWG that has performed well in a given application, such as bread, pizza dough, English muffins, or another desired bakery product, is combined in various known ratios with a starch. Mixtures containing specific ratios, such as 10:90, 40:60, 50:50, or 80:20 VWG to starch by weight are combined with a given amount of water and the viscosity of the resulting mixture is measured over time. In Example 1, a 40% VWG:60% starch mixture was found to be useful to discover both VWG development quality and the effect of the VWG on the starch. One of ordinary skill in the art will appreciate, however, that different VWG combined with different starches will have a different useful ratio for producing a useful standard curve, and that Example 1 illustrates how to identify the useful ratio for different VWG samples and starches.

The water absorption capacity of the VWG/starch mixture is assessed by adding water to the mixture and measuring the viscosity associated with the plateau indicated in FIG. 1. Higher water absorption causes higher dough viscosities. From the viscosity depicted by this plateau (between 2-8 minutes in FIG. 1), water absorptions of VWG:starch mixture may be calculated. The water absorption must be considered before running a rheology analysis. Once a water absorption has been chosen for a standard VWG, any VWG samples which are going to be compared to it should be run at the same water absorption. In the representative examples provided, initial mixing viscosity is targeted to be between 1-1.2 Newton-meters (Nm). Inaccurate conclusions can be reached if comparing viscosity profiles that were run either too dry or too diluted.

After the water amount is adjusted, the mixtures of VWG and starch at the chosen ratios of VWG to starch are used to generate rheology data. The correct water absorption will provide a viscosity profile (also referred to as a rheology profile) that displays the desired initial viscosity portion and gelatinization. This profile is then chosen as the standard mixture (see Figure I). Test mixtures using the same ratio as that of the standard mixture, but using VWG of unknown quality can then be tested and compared to the rheology profile of the standard mixture.

The first half of the profile data is identified by a steady increase in viscosity, followed by a plateau and usually (but not always) by the small glutenin peak. With increasing temperature, a small decline in viscosity occurs (see FIG. 1). The time at which the small glutenin peak occurs for the standard VWG mixture can be compared to the time at which the glutenin peak occurs in the sample mixture. Differences in the time at which the glutenin peaks occur can be used to identify the quality of the VWG sample. The presence and location of the glutenin peak is associated with variations in the processing conditions and/or the quality of the wheat used in manufacturing the VWG.

The gelatinization portion of the rheometric profile is identified by the steady increase in viscosity when the mixture is exposed to heat at or above the gelatinization temperature of the starch. When enzymes that degrade starch, called amylases, are present in the mixture, the torque produced during starch gelatinization will be reduced. As described herein the stirring rate is constant and torque is measured as resistance to that stirring motion. In most instances the presence of amylases is detected in VWG that has been extracted from sprouted wheat. Depending upon the desired properties of the end product the rheometric profile associated with the sample mixture may or may not produce the desired gelatinization portion of the rheometric profile.

Making Vital Wheat Gluten

Gluten is extracted from flour by washing out the starch with water. On an industrial scale, starch is the primary product, so cold water that does not impact the starch quality is the favored solvent. A slurry of wheat flour is stirred vigorously until the starch dissolves and the gluten consolidates into a mass that is collected by centrifugation, which is then carried through several stages in a continuous process. Filtration and/or a screw press remove the majority of the water and the residue is dried. In most processes, drying is accomplished by spraying the gluten into a flash drier or ring drier, set at temperatures between 50-70° C. In some processes, the final step includes sifting to make a more-finely powdered form.

The results and description provided herein indicate that rheology profiles can be used as part of a VWG production process, such as the one described above, as a method for quality control. For example, viscosity analysis, using the MIXOLAB® machine or other viscometer, can determine if there is a gluten quality problem due to acidic extraction water, heat damage, or the use of sprouted wheat for gluten extraction. Low pH extraction water will give an earlier glutenin peak (4-6 minutes) in the VWG development portion of the rheology curve (FIG. 3). Heat damage during drying will give a smaller, delayed glutenin peak such as shown in the profiles identified as 130° C. and 138° C. in FIG. 4. Gluten extracted from sprouted wheat will greatly reduce the expected viscosity due to starch gelatinization, as seen in FIG. 5. With such data, adjustments to wheat stock, extraction water pH and/or dryer temperature can then be made to avoid making poor-quality product.

As described above, one of the first steps of gluten production is to wash wheat flour with large quantities of water to dissolve away the starch. Once the starch has been removed, this water is then usually recycled. With continued use, the pH of this extraction water declines. If steps are not taken to raise the pH, the gluten product retains some of this residual acid. Too much residual acid decreases the strength of the VWG, as may be seen by an earlier glutenin peak and an earlier drop-off of the viscosity plateau. Using the methods provided herein the gluten can be tested and compared to a desirable standard. If the glutenin peak shifts to an unacceptably earlier time, the pH. of the wash water can be adjusted and production continued. Similarly, the gluten product is dried after the starch is separated. If the dryer temperature is too hot it will impact the viscosity profile. Using the methods described herein, upon identifying a shift in the glutenin peak to an unacceptably later time the dryer temperature can be adjusted down, thus allowing VWG quality to be maintained. The methods described herein also allow for the detection of amylases in the VWG. Too high of an amylase concentration can lead to VWG that will not display good baking properties. When a VWG sample having high amylase concentration is identified, the lot of VWG can be identified for sale to non-baking applications.

Since the methods provided herein assess the effects of process conditions on the final gluten product, they allow more cost efficient control of VWG production. The use of a rheology analysis to determine gluten quality allows an operator of a VWG production process to balance energy consumption, pH adjustment solution consumption, and VWG quality to arrive at the most cost-efficient production method allowable. For example, higher acid content in recycled extraction water can be tolerated by high strength VWG. A high-strength gluten product could also tolerate a higher drying temperature. Such control could provide a significant competitive advantage.

EXAMPLES

Example 1—VWG:Wheat Starch Ratio Determination

This example describes how to prepare a standard mixture for use in comparing sample mixtures that contain VWG having unknown qualities.

Flour samples were recreated by blending VWG and wheat starch. In normal flour, VWG levels are rarely above 15%. Gluten and starch mixtures with a VWG content higher than 80% did not wet out well, in other words the water absorption for this ratio was difficult to establish. The greater than 80% VWG/starch mixture are not described further as other ratios are more convenient. A number of different ratios of VWG and wheat starch were analyzed. Ratios of 10% VWG/90% wheat starch to 80% VWG/20% wheat starch (ratios are based on weight percent) gave curves that could be compared. A 40% VWG/60% wheat starch ratio was chosen for use in the remaining further examples. Wheat starch was used because it does not contain any of its own VWG to confound results. FIG. 1 shows data from a MIXOLAB© instrument when running a high quality gluten/wheat starch mixture that can be used as a standard.

After water is added to the gluten/starch mixture, the resulting dough is mixed at room temperature. Two VWG characteristics will affect the viscosity profiles during this section of the analysis. First, VWG will vary in water absorption capacity. The more water the VWG absorbs, the less free water is available to dilute the flour sample and the higher the viscosity plateau. Mixing stability is the second VWG characteristic that affects this early viscosity profile. Mixing stability is a measure of the time it takes for the initial viscosity plateau and to drop off to a lower level. Good quality VWG can be mixed for longer time periods without a reduction of viscosity and is said to have good mixing stability. Weak VWG will drop off in viscosity earlier, as the weaker gluten is unable to maintain its structure as the dough is torn during mixing. This viscosity reduction can be caused by either simple mixing (as with a farinograph) or by both mixing and increasing temperature (as with the MIXOLAB®).

For the purposes of these examples, the 40% VWG/60% Wheat starch mixtures are tested at a water absorption setting of 80% on a dry weight basis. The mixtures were added to the mix cell of the MIXOLAB® instrument and a standard program involving a kneading velocity of 80 RPM was initiated. For the first 8 minutes, the mix cell is held at 30° C. After 8 minutes, the mix cell temperature is raised at 4° C./minute to a final temperature of 90° C. After 7 minutes at 90° C., the cell temperature is dropped at 4° C./min to 50° C. and held there for 5 minutes (this standard program was used to generate FIGS. 1-5). The total analysis time was 45 minutes.

Example 2, Determining High Quality Gluten

This example describes the desired viscosity profile of a high quality gluten standard.

FIG. 1 shows the full rheology profile of a high quality gluten. The viscosity plateau is well established and does not drop off quickly (i.e. good mixing stability). The glutenin peak is well defined at the end of that plateau. The starch gelatinization peak is not significantly reduced by amylase activity. Sample B of FIG. 2 is also a good quality gluten. Samples C and D (FIG. 2) are progressively weaker glutens with shorter mixing stability times and no glutenin peak to extend those stability times. To compare gluten quality, one may either compare profiles as done in FIG. 2 or stability may be calculated from these profiles, thus allowing quantitative comparison. Stability is usually calculated by measuring the time the viscosity arrives at a given level to the time it dips under that viscosity (i.e. the length of the plateau identified in FIG. 1). Such calculations and/or rheology profiles can be used to establish specifications for VWG that is particularly useful for various end products.

Example 3, Assessing and Controlling the Effects of Extraction Water pH

This example describes the use of rheology profiles to identify acidic processing conditions used during VWG production.

To simulate the effects of acidic wash conditions in process water, either citric acid or sodium hydroxide was added to Sample B of FIG. 2 and the standard program provided in Example 1 was run. Unexpectedly, the glutenin peak that occurs at approximately 13 minutes gradually moves to earlier times when the sample is at a lower pH and later times for higher pH (FIG. 3). At pH<5, the stability of the gluten is affected and viscosity drops off rapidly after that peak. The time that the glutenin peak occurs is a good indicator of the pH of the VWG sample and its resultant effects on the VWG strength. The viscosity profile of Sample A of FIG. 2 closely matches that of Sample B when Sample B is adjusted to pH 4.5 (results not shown), indicating that this commercial sample may contain some residual acid, A pH analysis showed that Sample A indeed had a pH of 5.4, the lowest of the group of samples shown in FIG. 2. Low pH gluten does show reduced mixing strength and specifications (based on viscosity profiles) can be established for this process variable. In conclusion, the viscosity analysis of VWG proposed here can help determine the effects of extraction water on gluten quality.

Example 4, Assessing & Controlling Gluten Heat Damage

This example describes the use of rheology profiles to identify damage caused by applying excessive heat in the drying process of VWG.

If VWG attains too high a temperature as it dries, the protein denatures and becomes weaker, thus producing a low-stability VWG product. In order to assess if heat damage could be analyzed in the laboratory, small amounts of Sample A of FIG. 2 were placed in a lab oven for one hour at several different temperatures. After one hour of heating, each sample was removed, blended with wheat starch as described previously and run on the MIXOLAB® instrument using the standard program described in Example The resulting viscosity profiles that were generated are provided in FIG. 4.

These viscosity profiles show that heating caused a shift of the glutenin peak to later times and diminished the strength (Nm) of the initial plateau. For example, when Sample A was heated for one hour at 115° C., the glutenin peak was delayed by over two minutes. At 130° C. and 138° C., the glutenin peak disappears, causing a drop in mixing stability. According to these results, the poor quality of Samples C and D in FIG. 2 may be because they were overheated during the drying process. Sample C appears to have the equivalent amount of heat damage as Sample A after Sample A was K) heated for one hour at 130° C. Sample D appears to have the most heat damage, approximately the same as Sample A after one hour at 138° C. To assess the impact of heating during VWG processing, a sample can be obtained prior to the drying step in the process and the profile of this pre-dryer sample can be compared to the profile of the final, post-dryer sample. If the heat during drying is found to be impacting the VWG quality, the drying conditions can be altered. For example, the drying temperature can be reduced by 5, 10, or 15° C. and the throughput slowed to allow more residence time in the dryer, Example 5, Assessing & Controlling Gluten Effects on Starch This example describes the use of rheology profiles to identify the impact of VWG on starch.

VWG contains not only gluten and glutenin products, but also various other proteins such as carbohydrate-digesting enzymes that are produced by the wheat plant. By adding gluten samples to wheat starch and running a rheological analysis on the mixture, not only can protein performances be determined, but any effects of the gluten on wheat starch can be assessed as well. Once the initial, room temperature mixing of the dough has been accomplished, many viscometers can be programmed to gradually increase the temperature of the mixing cell. As the dough temperature climbs above 60° C., the wheat starch beings to gelatinize, increasing the viscosity of the dough significantly. Higher dough viscosities at this point indicate higher starch gelatinization strength. When the same wheat starch is used, this strength should be consistent unless the added gluten is affecting it. At these higher temperatures, amylases (which can be present in the VWG and therefore, in the dough) become very active, which reduces dough viscosity significantly.

For example, VWG was extracted from flour milled from sprouted wheat, which normally contains a high concentration of amylase. The effect of the amylase in the VWG on dough was then determined using a viscosity profile. FIG. 5 shows the viscosity profile of the sprouted wheat VWG sample compared to that of a normal gluten using the standard program described in Example 1. The effects on the starch strength during and after the gelatinization peak are obvious.

In order to better differentiate the levels of amylase in the VWG samples, a protocol to enhance amylase effects was established. This protocol increases the cell temperature quickly to 90° C. and holds it there for 35 minutes. Using this protocol any amylases that are present become active, which reduces starch viscosity. A 10% VWG/90% wheat starch mixture was used for this protocol. FIG. 6 compares four different gluten samples with different levels of sprouted wheat VWG. Sample #1 has the highest amylase concentration, causing the final starch viscosities to drop to the lowest level. Samples #2 and #3 have decreasing levels of amylase (or sprouted wheat inclusion) and attain higher viscosities at the end of the viscosity profile. Thus, this analysis could be used to identify and rank the level of amylase due to sprouted wheat in VWG samples. Wheat flour used to make gluten could also be screened by this same protocol to determine if sprouted wheat was used to make the flour.

Having illustrated and described the principles of the disclosure in multiple embodiments and examples, it should be apparent that the disclosure could be modified in arrangement and detail without departing from such principles. The disclosure encompasses all modifications coming within the spirit and scope of the following claims:

What is claimed is:

1. A method of producing flour with improved vital wheat gluten (VWG) quality, the method comprising:
    subjecting a standard VWG mixture containing a predetermined ratio of VWG to starch (VWG:starch) to rheometric analysis;
    determining, from the rheometric analysis of the standard VWG mixture, a standard viscosity plateau, a standard starch gelatinization portion, and a standard glutenin viscosity peak that is between the standard viscosity plateau and the standard starch gelatinization portion of the standard VWG mixture, wherein a standard rheometric profile comprises the standard viscosity plateau, the standard starch gelatinization portion, and the standard glutenin viscosity peak;
    extracting, using one or more processing conditions, a sample of VWG from a production supply of flour to obtain a sample VWG mixture;
    adding to the sample of VWG an amount of starch so that the sample VWG:starch ratio is the same as the predetermined ratio of VWG:starch ratio;
    subjecting the sample VWG mixture to rheometric analysis;
    determining, from the rheometric analysis of the sample VWG mixture, a sample viscosity plateau, a sample starch gelatinization portion, and a sample glutenin viscosity peak that is between the sample viscosity plateau and the sample starch gelatinization portion, wherein a sample rheometric profile comprises the sample viscosity plateau, the sample starch gelatinization portion, and the glutenin viscosity peak;
    comparing at least one of: (i) the standard viscosity plateau to the sample viscosity plateau and (ii) the standard glutenin viscosity peak to the sample glutenin viscosity peak; and
    adjusting the one or more processing conditions until the difference between at least one of: (i) the standard viscosity plateau and the sample viscosity plateau and (ii) the standard glutenin viscosity peak and the sample glutenin viscosity peak is less than or equal to 0.2 newton meters (Nm).

2. The method of claim 1, further comprising selecting the predetermined ratio of VWG:starch in the standard VWG mixture to be from about 10:90 to about 80:20 by weight.

3. The method of claim 1, further comprising selecting the predetermined ratio of VWG:starch in the standard VWG mixture to be about 10:90 by weight.

4. The method of claim 1, further comprising selecting the predetermined ratio of VWG:starch in the standard VWG mixture to be about 40:60 by weight.

5. The method of claim 1, wherein a difference between the standard glutenin viscosity peak and the sample glutenin viscosity peak indicates a pH less than 5.0 of wash water used during extraction of the sample VWG from the production supply of flour.

6. The method of claim 1, wherein a difference between the standard glutenin viscosity peak and the sample glutenin viscosity peak is an earlier glutenin viscosity peak in the sample rheometric profile.

7. The method of claim 1, wherein a difference between the standard glutenin viscosity peak and the sample glutenin viscosity peak indicates heat damage to the sample VWG mixture.

8. The method of claim 7, further comprising adding to the sample of VWG an amount of starch so the sample VWG to starch ratio is approximately the same as the standard VWG to starch ratio.

9. The method of claim 1, wherein a difference between the standard glutenin viscosity peak and the sample glutenin viscosity peak is a later glutenin viscosity peak in the sample rheometric profile.

10. The method of claim 1, wherein a difference between the standard starch gelatinization portion and the sample starch gelatinization portion indicates a different concentration of amylase in the standard VWG mixture as compared to the sample VWG mixture.

11. The method of claim 1, wherein a difference between the standard starch gelatinization portion and the sample starch gelatinization is a decrease in the starch gelatinization portion of the sample rheometric profile.

12. The method of claim 1, further comprising selecting the standard VWG mixture based on baking performance of the standard VWG mixture.

13. The method of claim 1, wherein the one or more processing conditions comprise washing the production supply of flour with acidic wash water and drying the sample VWG mixture extracted from the production supply of water at a drying temperature for a duration of time.

14. A method of producing flour with improved vital wheat gluten (VWG) quality, the method comprising:
    subjecting a standard VWG mixture to rheometric analysis, the standard VWG mixture comprising a standard VWG to starch ratio;
    determining, from the rheometric analysis of the standard VWG mixture, a standard viscosity plateau and a standard glutenin viscosity peak of the standard VWG mixture;
    extracting, using one or more processing conditions, a sample of VWG from a production supply of flour to obtain a sample VWG mixture, the sample of VWG comprising a sample VWG to starch ratio and the one or more processing conditions comprising washing the production supply of flour with wash water and drying the sample VWG mixture extracted from the production supply of water at a drying temperature for a duration of time;

subjecting the sample VWG mixture to rheometric analysis;

determining, from the rheometric analysis of the sample VWG mixture, a sample viscosity plateau and a sample glutenin viscosity peak of the standard VWG mixture; and adjusting the one or more processing conditions until the difference between at least one of: (i) the standard viscosity plateau and the sample viscosity plateau and (ii) the standard glutenin viscosity peak and the sample glutenin viscosity peak is less than or equal to 0.2 newton meters (Nm), wherein adjusting the one or more processing conditions comprises at least one of: increasing a pH of the wash water and reducing the drying temperature.

15. The method of claim 14, further comprising selecting the standard VWG to starch ratio to be between 10:90 and 80:20 by weight.

16. The method of claim 14, further comprising selecting the standard VWG to starch ratio to be about 40:60 by weight.

* * * * *